United States Patent
Furmanski et al.

(10) Patent No.: US 8,718,957 B2
(45) Date of Patent: May 6, 2014

(54) METHOD AND DEVICES FOR MONITORING FLOW CIRCUITS

(75) Inventors: Martin Furmanski, Malmö (SE); Anders Roslund, Malmö (SE); Bo Olde, Lund (SE); Kristian Solem, Kävlinge (SE)

(73) Assignee: Gambro Lundia AB, Lund (SE)

( * ) Notice: Subject to any disclaimer, the term of this patent is extended or adjusted under 35 U.S.C. 154(b) by 728 days.

(21) Appl. No.: 12/988,146

(22) PCT Filed: Apr. 16, 2009

(86) PCT No.: PCT/EP2009/054514
§ 371 (c)(1),
(2), (4) Date: Oct. 15, 2010

(87) PCT Pub. No.: WO2009/127683
PCT Pub. Date: Oct. 22, 2009

(65) Prior Publication Data
US 2011/0040502 A1    Feb. 17, 2011

Related U.S. Application Data

(60) Provisional application No. 61/045,642, filed on Apr. 17, 2008.

(30) Foreign Application Priority Data

Apr. 17, 2008    (SE) ........................... 0800890

(51) Int. Cl.
G01F 17/00    (2006.01)
(52) U.S. Cl.
USPC ........................................... 702/51
(58) Field of Classification Search
USPC ........................................... 702/51
See application file for complete search history.

(56) References Cited

U.S. PATENT DOCUMENTS

| 4,710,163 A | 12/1987 | Butterfield |
| 6,623,443 B1 | 9/2003 | Polaschegg |
| 2005/0010118 A1* | 1/2005 | Toyoda et al. ............... 600/486 |
| 2005/0051472 A1 | 3/2005 | Chionh et al. |
| 2005/0065459 A1 | 3/2005 | Zhang et al. |

FOREIGN PATENT DOCUMENTS

| JP | 63-65875 | 3/1988 |
| WO | WO 97/10013 A1 | 3/1997 |
| WO | WO 2005/062973 A2 | 7/2005 |

OTHER PUBLICATIONS

International Search Report from the European Patent Office for International Application No. PCT/EP2009/054514, mailing date Sep. 17, 2009.

* cited by examiner

Primary Examiner — Tung S Lau
Assistant Examiner — Xiuquin Sun
(74) Attorney, Agent, or Firm — Finnegan, Henderson, Farabow, Garrett & Dunner LLP

(57) ABSTRACT

A device is provided for monitoring the integrity of a flow circuit in fluid communication with a receptacle. The flow circuit includes a pumping device for transferring fluid through the flow circuit. The device operates according to a monitoring method in which a pressure signal is received from a pressure sensor, the pressure signal being indicative of fluid pressure in the receptacle or the flow circuit. The pressure signal is then processed for detection of a beating signal. The beating signal manifests itself as an amplitude modulation of the pressure signal and is formed by interference between pressure waves generated by a pulse generator associated with the receptacle and pressure waves generated by the pumping device. The integrity of the flow circuit is determined based at least partly on the presence or absence of the beating signal. The device and the flow circuit may be part of an apparatus for extracorporeal blood treatment, and the method may be implemented as a computer program product.

30 Claims, 9 Drawing Sheets

METHOD AND DEVICES FOR MONITORING FLOW CIRCUITS

CROSS REFERENCE TO RELATED APPLICATIONS

This application is a national phase application based on PCT/EP2009/054514 filed Apr. 16, 2009, which claims the benefit of Swedish Patent Application No. SE 0800890-6, filed Apr. 17, 2008, and U.S. Provisional Application No. 61/045,642, filed Apr. 17, 2008, the contents of all of which are incorporated herein by reference.

TECHNICAL FIELD

The present invention generally relates to monitoring of flow circuits, and in particular to monitoring the integrity of a flow circuit based on a pressure measurement. The present invention is i.a. applicable to flow circuits used in connection with extracorporal blood treatment, including extracorporeal blood flow circuits.

BACKGROUND ART

In extracorporeal blood treatment, blood is taken out of a patient, treated and then reintroduced into the patient by means of an extracorporeal blood flow circuit. Generally, the blood is circulated through the circuit by one or more pumping devices. The circuit is connected to the patient via a blood vessel access, typically in the form of one or more access devices, such as needles or catheters, which are inserted into a blood vessel of the patient. Such extracorporeal blood treatments include hemodialysis, hemodiafiltration, hemofiltration, plasmapheresis, etc.

In extracorporeal blood treatment, it is vital to minimize the risk for malfunctions in the extracorporeal blood flow circuit, since these may lead to a potentially life-threatening condition of the patient. Serious conditions may arise if the blood vessel access is disrupted, e.g. by an access device for blood extraction (e.g. an arterial needle/catheter) coming loose from the blood vessel, causing air to be sucked into the circuit, or by an access device for blood reintroduction (e.g. a venous needle/catheter) coming loose, causing the patient to be drained of blood within minutes. Other malfunctions may be caused by the blood vessel access becoming blocked or obstructed, e.g. by the access device being positioned too close to the walls of the blood vessel, or by tubing in the extracorporeal blood flow circuit being jammed or kinked.

To this end, an apparatus for extracorporeal blood treatment may include one or more surveillance devices that monitor the integrity of the blood flow circuit and issue an alarm and/or cause appropriate action to be taken whenever a potentially dangerous situation is detected. Such surveillance devices may operate on measurement signals from one or more pressure sensors in the circuit. Conventionally, the monitoring is carried out by comparing one or more measured pressure levels with one or more threshold values. For example, failure in the blood extraction may involve air being introduced into the circuit, whereby the measured pressure may approach atmospheric pressure, or the blood flow being blocked or obstructed, whereby the measured pressure may drop to a low level. A failure in the reintroduction of blood may be detectable as a decrease in the measured pressure. However, it may be difficult to set appropriate threshold values, since the pressure in the circuit may vary between treatments, and also during a treatment, e.g. as a result of the patient moving.

To increase the monitoring precision, WO 97/10013 proposes detecting, as one of several options, a heart signal in the measured pressure and using the heart signal as an indicator of the integrity of the circuit, in particular the integrity of the blood vessel access. The heart signal represents a pressure wave which is produced by the patient's heart and transmitted from the patient's circulatory system to the extracorporeal blood flow circuit via the blood vessel access. Malfunctions in the blood vessel access will disturb the transmission of the heart-generated pressure wave to the circuit, causing the heart signal to change or even disappear. The measured pressure also includes a strong pressure wave produced by the blood pump in the extracorporeal blood circuit. In WO 97/10013, the monitoring involves filtering a measured pressure signal to remove the frequency components that originate from the blood pump, and then detecting the heart signal by analysing the filtered pressure signal. However, if the heart signal is very weak and/or the heart beat frequency lies close to any of the frequency components of the blood pump, the heart signal may become undetectable and an erroneous alarm signal will be generated. Such a situation is not unlikely to occur since the patient's heart beat frequency, and often also the frequency of the blood pump, will vary during a treatment.

Corresponding needs to monitor the integrity of a flow circuit may arise in other fields of technology.

SUMMARY OF THE INVENTION

It is an object of the invention to at least partly overcome one or more of the above-identified limitations of the prior art. Specifically, it is an object to provide an alternative or complementary technique for monitoring the integrity of a flow circuit using a pressure measurement, preferably with an increased certainty of detecting a malfunction in the flow circuit.

This and other objects, which will appear from the description below, are at least partly achieved by means of methods, devices, a computer program product, and an apparatus according to the independent claims, embodiments thereof being defined by the dependent claims.

The present invention relates to techniques for monitoring the integrity of a flow circuit which comprises a pumping device and is in fluid communication with a receptacle. In its different aspects, one inventive concept of the present invention involves using the presence or absence of a beating signal in a pressure signal to evaluate the integrity of the flow circuit. The beating signal manifests itself as an amplitude modulation of the pressure signal and is formed by interference between pressure waves generated by the pumping device in the flow circuit and pressure waves generated by a pulse generator associated with the receptacle. Instead of trying to isolate a signal component generated by the pulse generator in the pressure signal, the presence of such a signal component is thus identified via the secondary effect of beating. Generally, beating is a phenomenon which is especially noticeable when two signals with closely spaced frequencies are added together. Thus, the beating signal detection is inherently well-suited to be used when the prior art technique fails, i.e. when the patient's heart frequency lies close to a frequency component of the pumping device.

In the context of present disclosure, "absence" of a beating signal may imply that the beating signal has disappeared, or at least that it has decreased sufficiently in magnitude compared to the beating signal deemed to be "present". The assessment of presence or absence may involve calculating an evaluation parameter based on the pressure signal and comparing the parameter value to a threshold value.

It is to be understood that the above-mentioned inventive concept may be used outside the field of extracorporeal blood treatment. Basically, it can be used for monitoring the integrity of any type of flow circuit in which a pumping device transfers a fluid to and/or from any type of receptacle (i.e. not only a patient). Any type of pulse generator may generate pressure waves in the receptacle, and any type of pressure sensor may be used for measuring the pressure in the flow circuit. As long as the pressure waves from the pulse generator can be detected, or have a sufficient magnitude, in the measured pressure in the flow circuit, the integrity of the flow circuit may be deemed to be intact.

A first aspect of the invention is a method for monitoring the integrity of a flow circuit in fluid communication with a receptacle, said flow circuit comprising a pumping device for transferring fluid through the flow circuit, said method comprising: receiving a pressure signal from a pressure sensor, said pressure signal being indicative of fluid pressure in the receptacle or the flow circuit; processing the pressure signal for detection of a beating signal formed by interference between pressure waves generated by a pulse generator associated with the receptacle and pressure waves generated by the pumping device; and determining the integrity of the flow circuit based at least partly on the presence or absence of the beating signal.

In one embodiment, the beating signal is detected by analyzing the pressure signal in the time domain.

In one embodiment, the method further comprises: obtaining one or more specific frequencies related to a pumping frequency of the pumping device; and creating at least one filtered pressure signal in which all but one of said specific frequencies are removed. The filtered pressure signal may then be processed for detection of the beating signal. The at least one specific frequency may comprise one or more of half the pumping frequency, the pumping frequency, and harmonics thereof.

In one embodiment, said processing comprises determining an envelope of the filtered pressure signal. Determining the envelope may comprise extracting an array of temporally sequential peak values from the filtered pressure signal. The processing may further comprise calculating at least one of a sum of derivatives and a variance based on the envelope.

In one embodiment, the method further comprises matching at least part of the filtered pressure signal against one or more predetermined signal patterns so as to detect the beating signal.

In one embodiment, the at least one specific frequency is obtained by at least one of analyzing the pressure signal in the frequency domain to identify said one or more specific frequencies; deriving a frequency measurement signal from the pumping device; and deriving a set value of a controller adapted to control the pumping frequency of the pumping device.

In one embodiment, the method further comprises: processing the pressure signal for detection of a signal component generated by the pulse generator, wherein the integrity of the flow circuit is determined also based on the presence or absence of said signal component.

In one embodiment, the processing of the pressure signal for detection of a beating signal is conditioned upon absence of said signal component in the pressure signal.

In one embodiment, the method further comprises: causing, in the absence of a beating signal, a predetermined change in the pumping frequency of the pumping device.

In one embodiment, the method further comprises: causing the pumping device to be temporarily inactivated, identifying the frequency of the pulse generator, and causing the pumping device to be activated with such a pumping frequency that all associated frequency components are offset from the frequency of the pulse generator.

In one embodiment, the processing is effected on a sequence of partially overlapping signal segments of the pressure signal, the length of each segment being given by a predetermined time window.

A second aspect of the invention is a method for monitoring the integrity of an extracorporeal blood flow circuit connected to a blood vessel of a patient, said extracorporeal blood flow circuit comprising a blood pumping device, said method comprising: receiving a pressure signal from a pressure sensor in the blood flow circuit; processing the pressure signal for detection of a beating signal formed by interference between pressure waves generated by the patient's heart and the blood pumping device, respectively; and determining the integrity of the blood flow circuit based at least partly on the presence or absence of the beating signal.

A third aspect of the invention is a device for monitoring the integrity of a flow circuit in fluid communication with a receptacle, said flow circuit comprising a pumping device for transferring fluid through the flow circuit, said device comprising: an input for a pressure signal from a pressure sensor, said pressure signal being indicative of fluid pressure in the receptacle or the flow circuit; and a signal processor comprising a first module configured to process the pressure signal for detection of a beating signal formed by interference between pressure waves generated by a pulse generator associated with the receptacle and pressure waves generated by the pumping device, said signal processor being configured to determine the integrity of the flow circuit based at least partly on the presence or absence of the beating signal.

In one embodiment, the first module is configured to detect the beating signal by analyzing the pressure signal in the time domain.

In one embodiment, the first module is further configured to obtain one or more specific frequencies related to a pumping frequency of the pumping device, and to create at least one filtered pressure signal in which all but one of said specific frequencies are removed.

In one embodiment, the first module is further configured to determine an envelope of the filtered pressure signal.

In one embodiment, the first module is further configured to determine the envelope by extracting an array of temporally sequential peak values from the filtered pressure signal.

In one embodiment, the first module is further configured to calculate at least one of a sum of derivatives and a variance based on the envelope.

In one embodiment, the first module is further configured to match at least part of the filtered pressure signal against one or more predetermined signal patterns so as to detect the beating signal.

In one embodiment, the signal processor comprises a second module which is configured to process the pressure signal for detection of a signal component generated by the pulse generator, wherein the signal processor is configured to determine the integrity of the flow circuit also based on the presence or absence of said signal component.

In one embodiment, the signal processor is configured to operate the first and second modules in sequence, such that the first module is operated only when the second module fails to detect said signal component in the pressure signal.

In one embodiment, the signal processor is configured to cause, in the absence of a beating signal, a predetermined change in the pumping frequency of the pumping device.

In one embodiment, the signal processor is configured to cause the pumping device to be temporarily inactivated, to identify the frequency of the pulse generator, and to cause the pumping device to be activated with such a pumping frequency that all associated frequency components are offset from the frequency of the pulse generator.

A fourth aspect of the invention is a device for monitoring the integrity of a flow circuit in fluid communication with a receptacle, said flow circuit comprising a pumping device for transferring fluid through the flow circuit, said device comprising: means for receiving a pressure signal from a pressure sensor, said pressure signal being indicative of fluid pressure in the receptacle or the flow circuit; means for processing the pressure signal for detection of a beating signal formed by interference between pressure waves generated by a pulse generator associated with the receptacle and pressure waves generated by the pumping device, respectively; and means for determining the integrity of the flow circuit based at least partly on the presence or absence of the beating signal.

A fifth aspect of the invention is a device for monitoring the integrity of an extracorporeal blood flow circuit connected to a blood vessel of a patient, said extracorporeal blood flow circuit comprising a blood pumping device, said device comprising: means for receiving a pressure signal from a pressure sensor in the blood flow circuit; means for processing the pressure signal for detection of a beating signal formed by interference between pressure waves generated by the patient's heart and the blood pumping device, respectively; and means for determining the integrity of the blood flow circuit based at least partly on the presence or absence of the beating signal.

A sixth aspect of the invention is a computer program product comprising instructions for causing a computer to perform the method according to the first or second aspect.

A seventh aspect of the invention is an apparatus for extracorporeal blood treatment, comprising an extracorporeal blood flow circuit including a blood pumping device, a pressure sensor arranged in the blood flow circuit, and the device according to the third, fourth or fifth aspect.

Still other objectives, features, aspects and advantages of the present invention will appear from the following detailed description, from the attached claims as well as from the drawings.

BRIEF DESCRIPTION OF THE DRAWINGS

Embodiments of the invention will now be described in more detail with reference to the accompanying schematic drawings.

DETAILED DESCRIPTION OF EMBODIMENTS OF THE INVENTION

Figure 1:
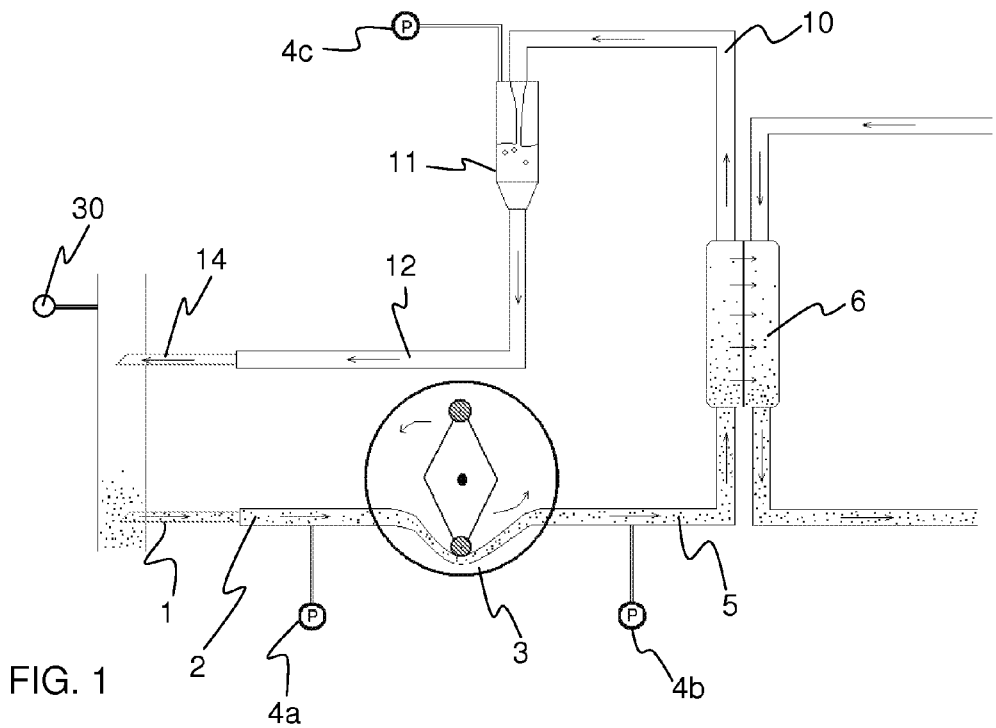
FIG. 1 is a schematic view of a system for hemodialysis treatment including an extracorporeal blood circuit.

In the following, embodiments of the inventions will be described in the context of extracorporeal blood treatment. However, the disclosed embodiments as well as the underlying inventive concepts are applicable outside this context, as will be further clarified in the closing sections of the description.

Throughout the following description, like elements are indicated by corresponding reference numerals.

FIG. 1 shows an extracorporeal blood circuit of the type which is used in a dialysis machine. The circuit comprises an arterial needle 1 and an arterial tube segment 2 which connects the arterial needle 1 to a blood pump 3 which may be of peristaltic type, as indicated in FIG. 1. At the inlet of the pump there is a pressure sensor 4a (hereafter referred to as arterial sensor) which measures the pressure before the pump in the arterial tube segment 2. The blood pump 3 forces the blood, via a tube segment 5, to a dialyser 6. Many dialysis machines are additionally provided with a pressure sensor 4b that measures the pressure between the blood pump 3 and the dialyser 6, the so-called system pressure. The blood is lead via a tube segment 10 from the dialyser 6 to a venous drip chamber or deaeration chamber 11 and from there back to the patient via a venous tube segment 12 and a venous needle 14. The chamber 11 is provided with a pressure sensor 4c (hereafter referred to as venous sensor) that measures the pressure in the venous drip chamber. Both the arterial needle 1 and the venous needle 14 are connected to the patient by means of a blood vessel access. The blood vessel access may be of any suitable type, e.g. a fistula, a Scribner-shunt, one or more catheters, a graft, etc. For the purpose of the following discussion, the blood vessel access is assumed to be a fistula.

When the blood passes the arterial needle 1, which has a small cross-sectional area in order not to damage the fistula, the pressure sinks to between about −200 to −50 mm Hg relative to the surrounding atmosphere, which is measured by the arterial sensor 4a. The pressure rises in the pump 3, said pressure being measured by the system sensor 4b. In the dialyser 6, the pressure drops due to the flow resistance therein and the pressure after the dialyser is measured with the venous sensor 4c, which normally is connected to measure the pressure in the venous drip chamber 11. The pressure in the chamber 11 is normally between +50 to +150 mm Hg. Finally the blood is released to the fistula via the venous needle 14, whereby a pressure drop occurs in the needle due to the flow through its small cross-section.

The aforementioned pressure conditions vary considerably from patient to patient and can even vary for one and the same patient between different treatment sessions, as well as during one and the same treatment session. It is therefore difficult to set up threshold values for the pressure sensors, in order to indicate different error/malfunction conditions. In many dialysis machines, one or more of said pressure detectors 4a-4c are not present. However, there will be at least one venous pressure sensor. As discussed by way of introduction, it may be vital to monitor the integrity of the blood circuit, and in particular the blood vessel access with respect to malfunction in the injection and/or extraction of blood therethrough.

FIG. 1 further shows an optional pulse meter 30 separately attached to the patient to measure the heart pulse rate. The pulse meter 30 may be any of a pulse watch, pulse oximeter, electrocardiograph, echocardiogram, microphone, pulse belt, any form of plethysmography, photoplethysmography (PPG), blood pressure cuff, or any combinations thereof.

Figure 2:
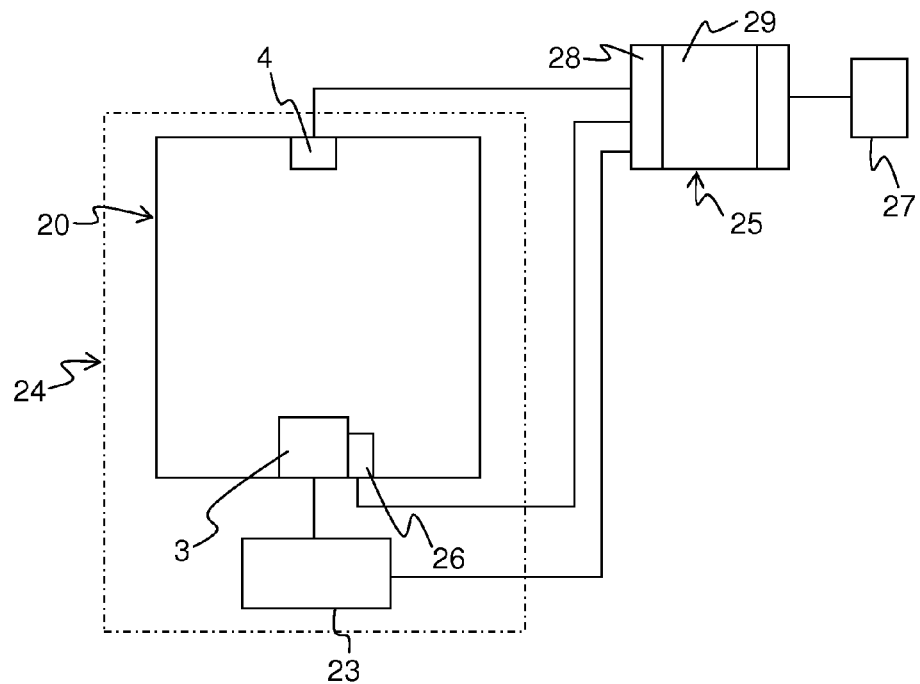
FIG. 2 is a schematic view of an extracorporeal blood circuit connected to a surveillance device.

FIG. 2 is yet another schematic illustration of an extracorporeal blood circuit 20, comprising the blood pump 3 and a pressure sensor 4 (representing one of sensors 4a-4c in FIG. 1). A control unit 23 is provided, i.a., to control the blood flow in the circuit 20 by controlling the revolution speed of the blood pump 3. The blood circuit 20 and the control unit 23 may form part of an apparatus 24 for extracorporeal blood treatment, such as a dialysis machine. Although not shown or discussed further it is to be understood that such an apparatus 24 performs many other functions, e.g. controlling the flow of dialysis fluid, controlling the temperature and composition of the dialysis fluid, etc.

A surveillance/monitoring device 25 is connected to the apparatus 24 and is configured to monitor the integrity of the blood circuit 20, specifically by monitoring the presence of a signal component originating from the patient's heart in a blood pressure signal. Absence of such a signal component is taken as an indication of a failure in the integrity of the blood circuit 20, and brings the device 25 to activate an alarm and/or stop the blood flow by stopping the blood pump 3. The surveillance device 25 is at least connected to the apparatus 24 to receive a signal representative of the measurement signal of the pressure sensor 4. As indicated in FIG. 2, the device 25 may also be connected to the control unit 23. Alternatively or additionally, the device 25 may be connected to a measurement device 26 for indicating the frequency of the blood pump 3. The device 25 is tethered or wirelessly connected to a local or remote device 27 for generating an audible/visual/tactile alarm or warning signal. The surveillance device 25 and/or the alarm device 27 may alternatively be incorporated as part of the apparatus 24.

In FIG. 2, the surveillance device 25 comprises a data acquisition part 28 for pre-processing the incoming signal(s), e.g. including an A/D converter with a required minimum sampling rate and resolution, one or more signal amplifiers, one or more filters to remove undesired components of the incoming signal(s), such as offset, high frequency noise and supply voltage disturbances.

In the examples given herein, the data acquisition part 28 comprises a DAQ card USB-6210 from National Instruments with a sampling rate of 1 kHz and resolution of 16 bits, an operation amplifying circuit AD620 from Analog Devices, a high-pass filter with a cut-off frequency of 0.03 Hz (i.a., for removal of signal offset) together with a low-pass filter with a cut-off frequency of 402 Hz (i.a., for removal of high frequency noise). To obtain a low convergence time, a high-order filter (order 3-4) is used for the high-pass filter. Furthermore, the data acquisition part 28 may include an additional fixed band-pass filter with upper and lower cut-off frequencies of 0.5 Hz and 2.7 Hz, respectively, which corresponds to heart pulse rates between 30 and 160 beats per minute. This filter may be used to suppress disturbances outside the frequency interval of interest.

After the pre-processing in the data acquisition part 28, the signal from the pressure sensor 4 is provided as input to a data analysis part 29, which executes the actual monitoring process. FIG. 3(a) shows an example of such a pre-processed pressure signal in the time domain, and FIG. 3(b) shows the corresponding power spectrum, i.e. the pressure signal in the frequency domain. The power spectrum reveals that the detected pressure signal contains a number of different frequency components emanating from the blood pump 3. In the illustrated example, there is a frequency component at the base frequency ($f_0$) of the blood pump (at 1.5 Hz in this example), as well as its harmonics $2f_0$, $3f_0$ and $4f_0$. The base frequency, also denoted pumping frequency in the following, is the frequency of the pump strokes that generate pressure waves in the blood circuit. For example, in a peristaltic pump of the type shown in FIG. 1, two pump strokes are generated for each full revolution of the rotor. FIG. 3(b) also indicates the presence of a frequency component at half the pumping frequency ($0.5f_0$) and harmonics thereof, in this example at least $f_0$, $1.5f_0$, $2f_0$ and $2.5f_0$. FIG. 3(b) also shows a heart signal (at 1.1 Hz) which in this example is approximately 40 times weaker than the blood pump signal at the base frequency $f_0$.

The embodiments to be described in the following have been designed to detect malfunction of the blood circuit 20 within a given minimum reaction time. Segments of the pressure signal are analysed by the data analysis part 29 to detect such malfunction. Longer signal segments result in a high monitoring accuracy but a long reaction time. Conversely, shorter signal segments result in a small reaction time, but at the expense of a reduced monitoring accuracy. As a compromise, the pressure signal is preferably analysed in overlapping fixed-length time windows, i.e. overlapping signal segments are analysed. For example, the time window may be shifted by one second in the incoming pressure signal, such that successive signal segments overlap but for one second of data. In the examples given herein, a time window of 20 seconds is used to define signal segments to be analysed.

Figure 4:
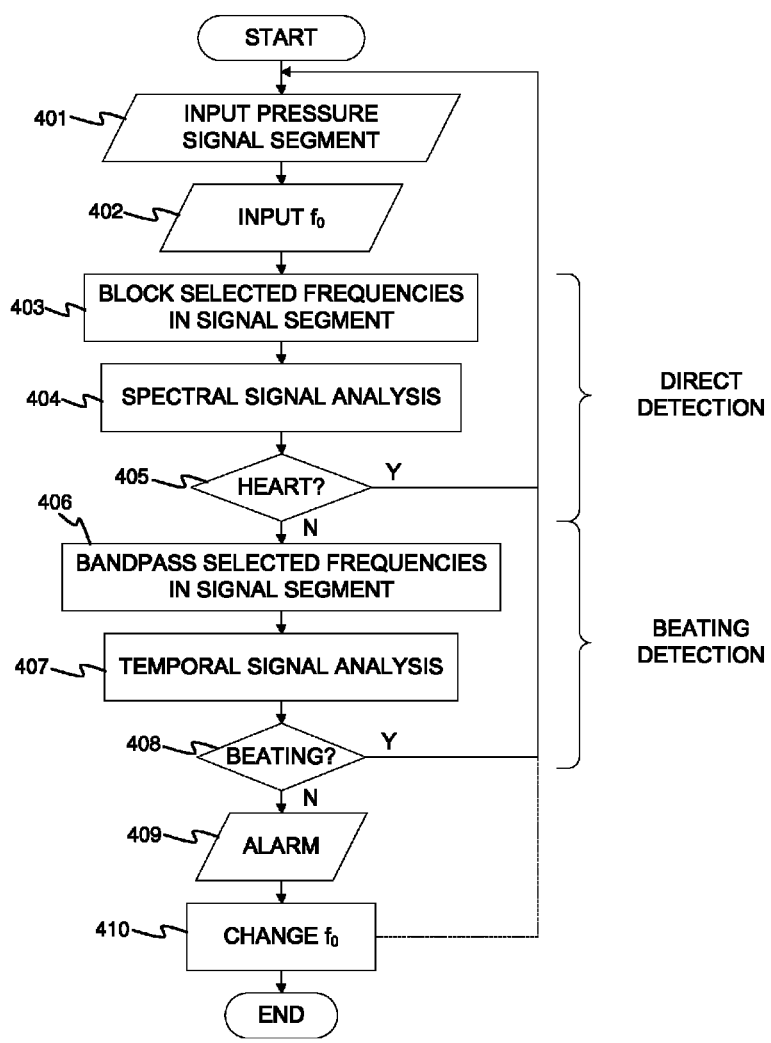
FIG. 4 is a flow chart of a process for monitoring the integrity of a blood circuit.
Figure 11:
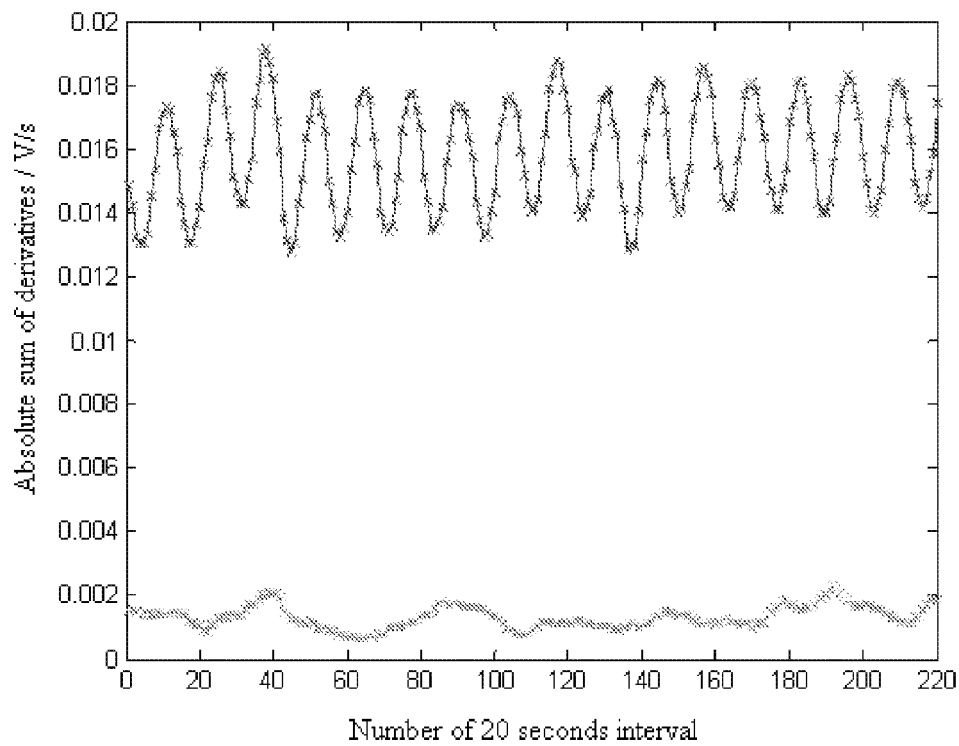
FIG. 11 is a plot of the sum of derivatives as a function of time, calculated from envelopes with and without a heart signal.
Figure 12:
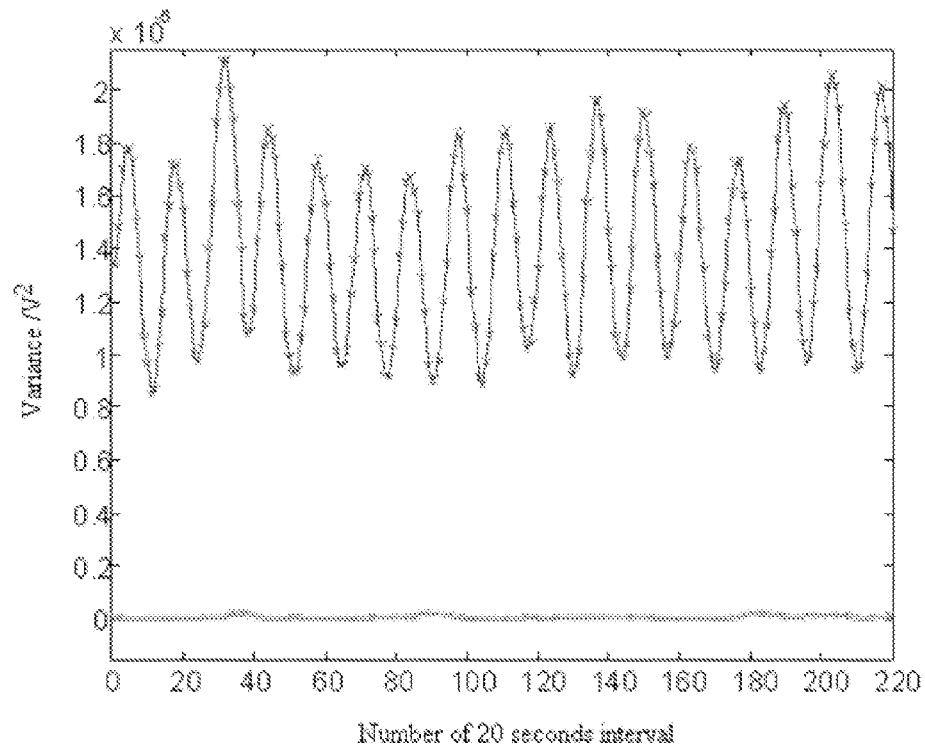
FIG. 12 is a plot of variance as a function of time, calculated from envelopes with and without a heart signal.

In a variant, signal segments of different lengths may be processed/analysed to detect malfunction of the blood circuit. Such signal segments may or may not be overlapping. In one such embodiment, the length of the signal segment (time window) may be adaptively set as a function of the blood flow rate, e.g. given by the revolution speed or pumping frequency of the blood pump. For example, since the impact of a potential malfunction may be less severe at low blood flow rates, the length of the signal segment may be increased with decreasing blood flow rate. In another embodiment, signal segments of different length may be processed/analysed in parallel or sequence to detect malfunction of the blood circuit. For example, when a combination of detection methods is used to detect malfunction (e.g. as shown in FIG. 4, see below), the different detection methods may operate on signal segments of different length. Further, if one and the same method uses a combination of evaluation parameters to detect malfunction (e.g. as shown in FIGS. 11 and 12, see below), the different evaluation parameters may be derived by processing/analysing signal segments of different length.

FIG. 4 is a flow chart for a data analysis or monitoring process according to an embodiment of the present invention. The illustrated process implements a combination of detection methods to monitor the integrity of the blood circuit. One detection method ("direct detection") involves detecting a frequency component emanating from the patient's heart in the pressure signal. Another detection method ("beating detection") involves detecting an amplitude modulation (beating signal) in the pressure signal, the amplitude modulation being caused by interference between pressure waves originating from the patient's heart and the blood pump. These detection methods will be described in further detail below, but first the overall operation of the process will be briefly outlined.

The monitoring process starts by inputting a signal segment of the pressure signal (step 401), as well as information on the base frequency ($f_0$) of the blood pump (step 402). This frequency information may be derived from processing of the pressure signal itself. Alternatively, it may be derived from a signal generated by a dedicated measurement device (cf. 26 in FIG. 2), or from a signal indicative of a set value or actual value used by the control unit (cf. 23 in FIG. 2). It is to be understood that step 402 need not be executed for every iteration of the monitoring process.

Figure 3:
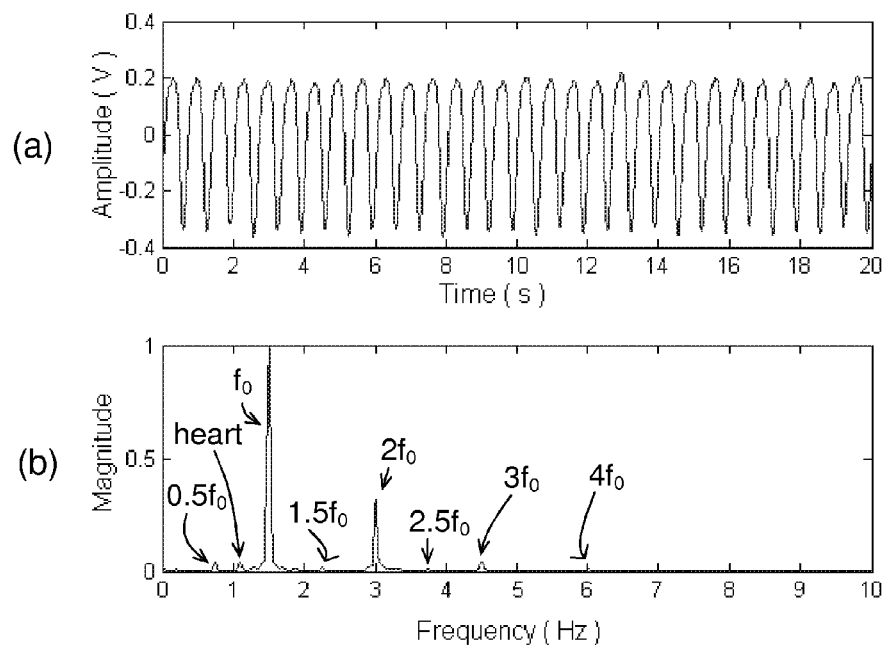
FIG. 3(a) is a plot in the time domain of a venous pressure signal containing both pump frequency components and a heart signal.
FIG. 3(b) is a plot of the corresponding signal in the frequency domain.

The direct detection method involves steps 403-405, in which the signal segment is processed so as to block one or more of the frequency components (see $0.5f_0$, $f_0$, $1.5f_0$, $2f_0$, $2.5f_0$, $3f_0$ and $4f_0$ in FIG. 3) related to the blood pump. Typically, step 403 is designed to effectively "clean" the signal segment from all frequency components emanating from the blood pump. In step 404, the signal segment is analysed in the frequency domain to identify any remaining frequency component emanating from the patient's heart. If such a heart component is detected in step 405, the monitoring is returned to step 401, in which a new pressure signal segment is inputted for processing. As mentioned above, this new signal segment may partially overlap the preceding signal segment. If no heart component is detected in step 405, the monitoring proceeds to beating detection. The lack of a heart component may result from a malfunction of the blood circuit or by the heart component being too weak and/or too close in frequency to any of the frequency components of the blood pump.

The beating detection method involves steps 406-408, in which the signal segment is processed so as to identify a beating signal caused by interference between pressure waves originating from the heart and the blood pump, respectively. The beating signal is perceived as periodic variations in signal amplitude with a frequency equal to the difference in frequency between these two pressure waves. Thus, instead of searching for the heart pulse itself in the pressure signal, the beating detection looks at the effects of the heart pulse on the pressure signal in the time domain.

In step 406, the signal segment is processed to remove all frequencies except for one or more selected frequency bands. Each such selected frequency band is a band surrounding only one of the frequency components (see $0.5f_0$, $f_0$, $1.5f_0$, $2f_0$, $2.5f_0$, $3f_0$ and $4f_0$ in FIG. 3) related to the blood pump. This selective bandpass filtering may be effected to facilitate the detection of the beating signal. The pressure wave from the heart is generally much smaller (typically 20-200 times) than the pressure wave from the blood pump, so a potential beating wave will be weak and possibly difficult to detect. Typically, all frequencies outside one such selected frequency band are removed from the signal segment, whereupon the resulting filtered signal segment is analysed in the time domain for detection of a beating signal (step 407). If the blood pump is known to produce a number of frequency components (as shown in FIG. 3), step 406 results in a set of filtered signal segments, each including only frequencies around one of these frequency components. These filtered signal segments may be generated in parallel and then analysed in step 407. Alternatively, filtered signal segments may be generated in sequence, based on a given order of blood pump frequency components. Each filtered signal segment may be passed on to step 407 for analysis before another filtered signal segment is generated, such that the generating of filtered signal segments is interrupted as soon as a beating signal is detected.

In yet another embodiment, the heart pulse rate is known. In such a situation, step 406 may be limited to generating only one filtered signal segment, which includes only frequencies around the frequency component that lies closest to the known heart frequency. The heart pulse rate may be given by a pulse meter 30 of FIG. 1 incorporated in the blood circuit or separately attached to the patient. Alternatively, the heart pulse rate may be derived in a preceding or concurrent step, in which the pressure signal is analysed in the time domain or frequency domain to identify the heart frequency, i.e. the heart pulse rate.

For example, the heart frequency could be derived by step 406 in a preceding iteration of the monitoring process. Optionally, this pressure signal may be obtained while the blood pump is switched off in order to remove any interfering frequency components emanating from the blood pump. Yet another alternative is to derive the heart pulse rate by analysing a pressure signal from another pressure sensor in the blood circuit. For example, if the beating detection method is based on the pressure signal from the venous sensor (4c in FIG. 1), the heart pulse rate may be derived from a pressure signal from the arterial sensor (4a in FIG. 1). In many blood circuits, the pressure waves from the heart may be stronger, and the pressure waves from the blood pump weaker, on the arterial side compared to the venous side, facilitating determination of the heart pulse rate based on the pressure signal from the arterial sensor.

The selective bandpass filtering of step 406 may use a fixed width of the frequency band(s), which is set in view of a desired performance of the beating detection method, typically the maximum frequency spacing between a heart pulse and a pump frequency component that should result in a beating signal. For example, the frequency bands used by the beating detection method may be small compared to the spacing of the pump frequency components, if the beating detection method is used in combination with another detection method (e.g. the direct detection method) which is capable of detecting presence/absence of a heart signal in specific frequency regions in between these frequency components. In other situations, the frequency bands may have about the same total width as the spacing of the pump frequency components, or the frequency bands of adjacent pump frequency components may even overlap. In another embodiment, the width of the frequency band(s) may be adaptively set as a function of a previously determined heart frequency. For example, the width may be reduced as the heart frequency approaches one of the pump frequency components. As mentioned above, the heart frequency may e.g. be derived from a separate pulse rate meter, another pressure sensor, or in a preceding iteration of the monitoring process.

If a beating signal is detected in step 408, the monitoring is returned to step 401, in which a new pressure signal segment is inputted for processing. If no beating signal is detected in step 408, the monitoring proceeds to activate an alarm that indicates a malfunction of the blood circuit, or at least a warning that such a malfunction may have occurred (step 409). Concurrently with activating the alarm/warning, the process may proceed to step 410 in which the pumping frequency is changed, whereupon the monitoring process may return to step 401 to continue to monitor the integrity of the blood circuit. If a heart component/beating signal is discovered during subsequent iteration(s) of the monitoring process, the alarm/warning may be shut off. Alternatively, to minimize the number of false alarms, the alarm/warning may be activated only if the monitoring process fails to detect the heart signal both before and after such a change in pumping frequency.

In one embodiment of step 410, the pump is kept operative, but its pumping frequency is changed. In one variant, the pumping frequency is lowered in order to reduce the blood flow and thereby minimize any blood loss caused by the potential malfunction that has been detected. In another variant, the pumping frequency is actively shifted such that its frequency components are non-coincident with its previous frequency components. For example, the base frequency could be shifted by a fraction of the spacing between the frequency components originating from the pump. In the example of FIG. 3, this would mean a fraction of $0.5f_0$. Typically, the shift represents a reduction in the pumping frequency.

In another embodiment of step 410, the pump is shut-down (i.e. $f_0=0$) to remove the interference from the blood pump while also minimizing any blood loss caused by the potential malfunction that has been detected. In a variant of such an embodiment, step 410 also involves identifying the frequency of the heart while the blood pump is shut-down, and then re-starting the blood pump with a pumping frequency shifted from the thus-identified heart frequency. The heart frequency may be identified from the pressure signal, e.g. using the spectral signal analysis of step 404.

In a further embodiment of step 410, the heart pulse rate is known as described above, for instance from an independent source 30 of FIG. 1. The heart pulse rate may be given by a pulse meter 30 incorporated in the blood circuit or separately attached to the patient. In a variant of such an embodiment, step 410 also involves shifting the pumping frequency of the blood pump from the identified heart frequency. Thus, causing the pumping device to be activated with such a pumping frequency that all associated frequency components are offset from the frequency of the pulse generator. The pulse meter 30 may be any of a pulse watch, pulse oximeter, electrocardiograph, echocardiogram, microphone, pulse belt, any form of plethysmography, photoplethysmography (PPG), blood pressure cuff, or any combinations thereof.

Figure 5:
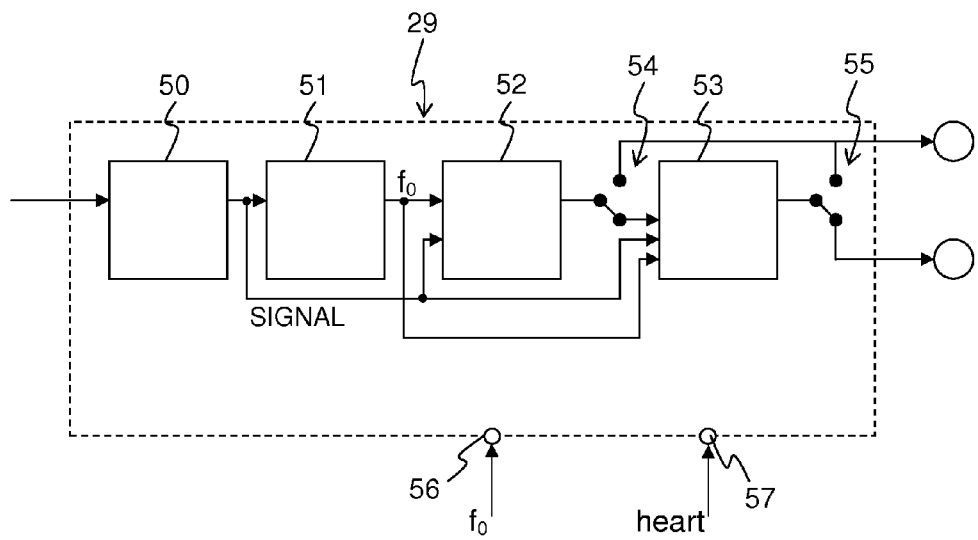
FIG. 5 is a block diagram of a data analyser for executing the process of FIG. 4.

FIG. 5 is a block diagram of the data analysis part (cf. 29 in FIG. 2) which is configured to carry out the monitoring process shown in FIG. 4. In the illustrated embodiment, the data analysis part includes a storage block 50, a pump frequency determination block 51, a direct detection block 52, a beating detection block 53, and switching blocks 54, 55 for connecting the output of the direct detection block 52 and the beating detection block 53 to an alarm device. Although not shown, a control block may be provided to synchronize the operation of the blocks 50-55.

The data analysis part 29 may be implemented by software running on a processing device, such as a general- or special-purpose computer device or a programmed microprocessor. The storage block 50 may be a volatile or non-volatile memory of such a computer device, whereas the other blocks 51-55 may be implemented by software instructions. However, it is conceivable that some or all blocks are fully or partially implemented by dedicated hardware, such as an FPGA, an ASIC, or an assembly of discrete electronic components (resistors, capacitors, operational amplifier, transistors, etc), as is well-known in the art.

The storage block 50 is operated to store the incoming pressure signal as a sequence of data samples. The other blocks 51-53 are then operated to receive or retrieve segments of the stored pressure signal from the storage block 50. The storage block 50 thus buffers the incoming pressure signal, allowing overlapping or non-overlapping signal segments to be individually processed and analysed. The storage block 50 may, e.g., be implemented as a plurality of linear buffers or as a circular buffer.

Block 51 is configured to determine the frequency of the blood pump based on a signal segment. An example of an algorithm used by such a block will be further described below.

Block 52 implements the direct detection steps 403-405 (FIG. 4), based on an estimated pumping frequency provided by the pump frequency determination block 51. If the outcome of the determination step 405 is negative, i.e. no heart component is found, switching block 54 is operated to activate block 53. If a heart component is found, switching block 54 may be operated to provide a positive status indication to the alarm device, and a new signal segment may be received or retrieved by blocks 51, 52.

Block 53 implements the beating detection steps 406-408 (FIG. 4), again based on the estimated pumping frequency. If the outcome of determination step 408 is negative, i.e. no beating signal is detected, switching block 55 is operated to provide a negative status indication to the alarm device, which issues an alarm. If a beating signal is found, switching block 55 may be operated to provide a positive status indication to the alarm device, and a new signal segment may be received or retrieved by the blocks 51, 52.

In FIG. 5, the data analysis part also includes an input 56 for receiving a signal indicative of the pumping frequency (e.g. from the measurement device 26 or the control unit 23 in FIG. 2). As discussed in relation to step 410 (FIG. 4), frequency information derived from this signal may supplement or replace the frequency determined by block 51.

FIG. 5 also indicates the provision of an input 57 for a measurement signal indicative of the patient's heart frequency, e.g. to be used by block 53 when executing step 406 and/or step 410.

An exemplifying operation for each of the blocks 51-53 will now be described, starting with the pump frequency determination block 51.

The pump frequency determination block 51 is configured to calculate a power spectrum from a pressure signal segment, and identify the base pumping frequency in the power spectrum. The power spectrum can be calculated in any known way, e.g. by operating a DFT (Discrete Fourier Transform) or an FFT (Fast Fourier Transform) on the pressure signal segment. The base pumping frequency may be identified as the frequency of the largest peak in the power spectrum, or at least among one of the largest peaks.

If the resolution of the power spectrum is low, special measures may be employed to increase the accuracy of the estimated frequency. The resolution is dependent on the sampling frequency $f_s$ and the number of samples N in the signal segment as $f_s/N$. In one example, signal segments of 20 seconds are sampled at 10 Hz, with a resolution of 0.05 Hz. This accuracy may be inadequate for the processing in the direct detection block 52 and/or beating detection block 53. To increase the accuracy, the signal segment may be bandpass filtered in a narrow range around the estimated frequency derived from the power spectrum, resulting in a comparatively noiseless and sinusoid-like signal segment. A precise estimation of the base frequency can then be obtained by determining the period of the filtered signal segment in the time domain, e.g. by adapting a sinusoid to the filtered signal and identifying the time difference between zero-crossings.

The direct detection block 52 may be configured to operate a comb filter and/or a combination of band-stop filters, typically cascade coupled, on the pressure signal segment to block out all frequency components originating from the blood pump. Alternatively, such blocking may be achieved by the use of one or more adaptive filters, e.g. as disclosed in aforesaid WO 97/10013. The direct detection block 52 then calculates the power spectrum of the filtered signal segment, e.g. using DFT or FFT, identifies the highest peak in the power spectrum, and assesses whether this peak is significant enough or not. For example, a relation may be formed between the square of the peak value ($f_k$) and the mean of the squared power spectrum values (excluding the peak value), given by $$\frac{f_k^2}{\frac{1}{N-1}\sum_{i=0}^{N-2} f_i^2}.$$

If this relation exceeds a predetermined reference level, it is determined that a heart pulse is present, otherwise not. This reference level may vary between different flow rates in the system (e.g. represented by the base frequency of the blood pump). Thus, the direct detection block 52 may access a database that relates reference levels to base frequencies for the decision making.

Figure 6:
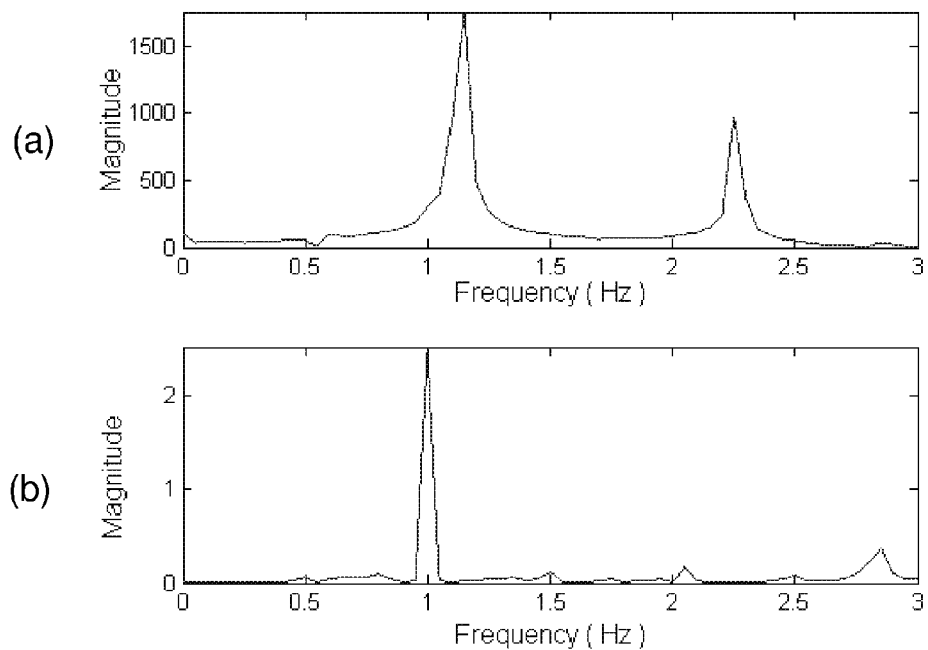
FIGS. 6(a) and 6(b) are plots showing the power spectrum of a pressure signal before and after processing by a direct detection module in the data analyser in FIG. 4.

FIG. 6($a$) shows a power spectrum of the pressure signal segment obtained for a blood pumping frequency of 1.13 Hz and a heart pulse at 1 Hz, with the relative magnitude between the heart pulse and the pumping pulse being 1:60. FIG. 6($b$) shows the power spectrum of the same signal segment after filtering by the direct detection block. In this case, the frequency components of the blood pump have been removed, leaving the heart pulse and some noise.

Figure 7:
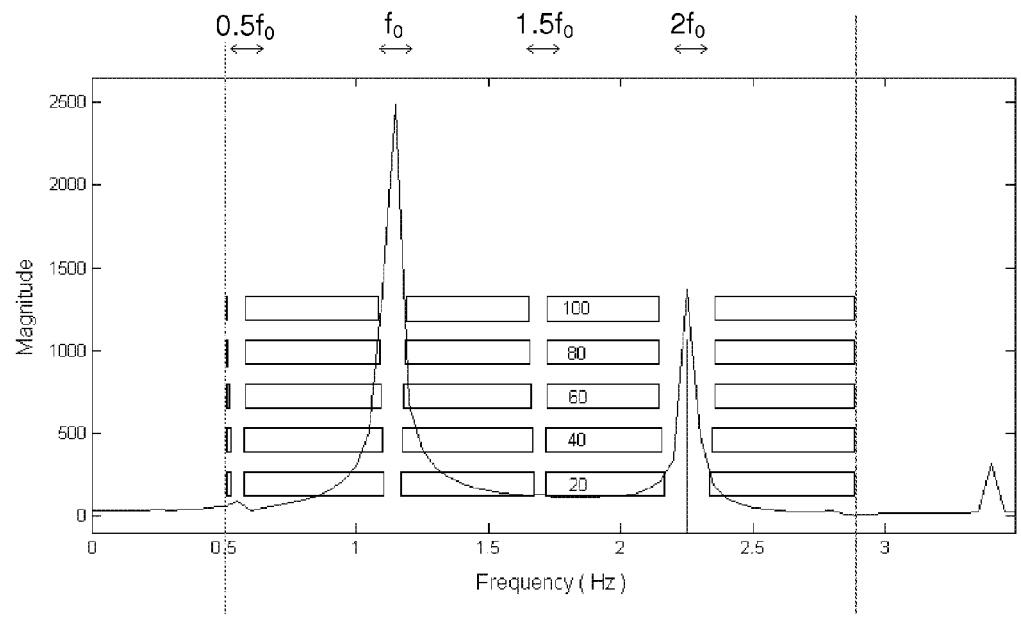
FIG. 7 is a diagram illustrating the performance of a direct detection module, for different relative magnitudes between the blood pulse and the heart pulse.

FIG. 7 is an example of frequency and amplitude ranges in which a heart pulse is detectable using the aforesaid direct detection block 52. The dotted vertical lines indicate the frequency range of a normal heart, and the horizontal bands indicate the frequencies at which a heart pulse could be detected in a system using a pumping frequency of 1.13 Hz. The five rows of horizontal bands represent different relative magnitudes between the blood pump and heart pulses, ranging from 20:1, 40:1, 60:1, 80:1 and 100:1 from the bottom row to the top row. Clearly, there are large zones around the frequency components of the blood pump in which a heart signal is not detectable in the direct detection block, and these zones widen with decreasing relative magnitude of the heart pulse.

The beating detection block 53 is configured to filter the signal segment with respect to a set of passbands, each containing one frequency component of the blood pump. Each resulting filtered signal segment is essentially a sinusoid. If the frequency of the heart lies within one of these passbands, then the corresponding filtered signal segment will have a waveform not to be found in any of the other filtered signal segments.

Figure 8:
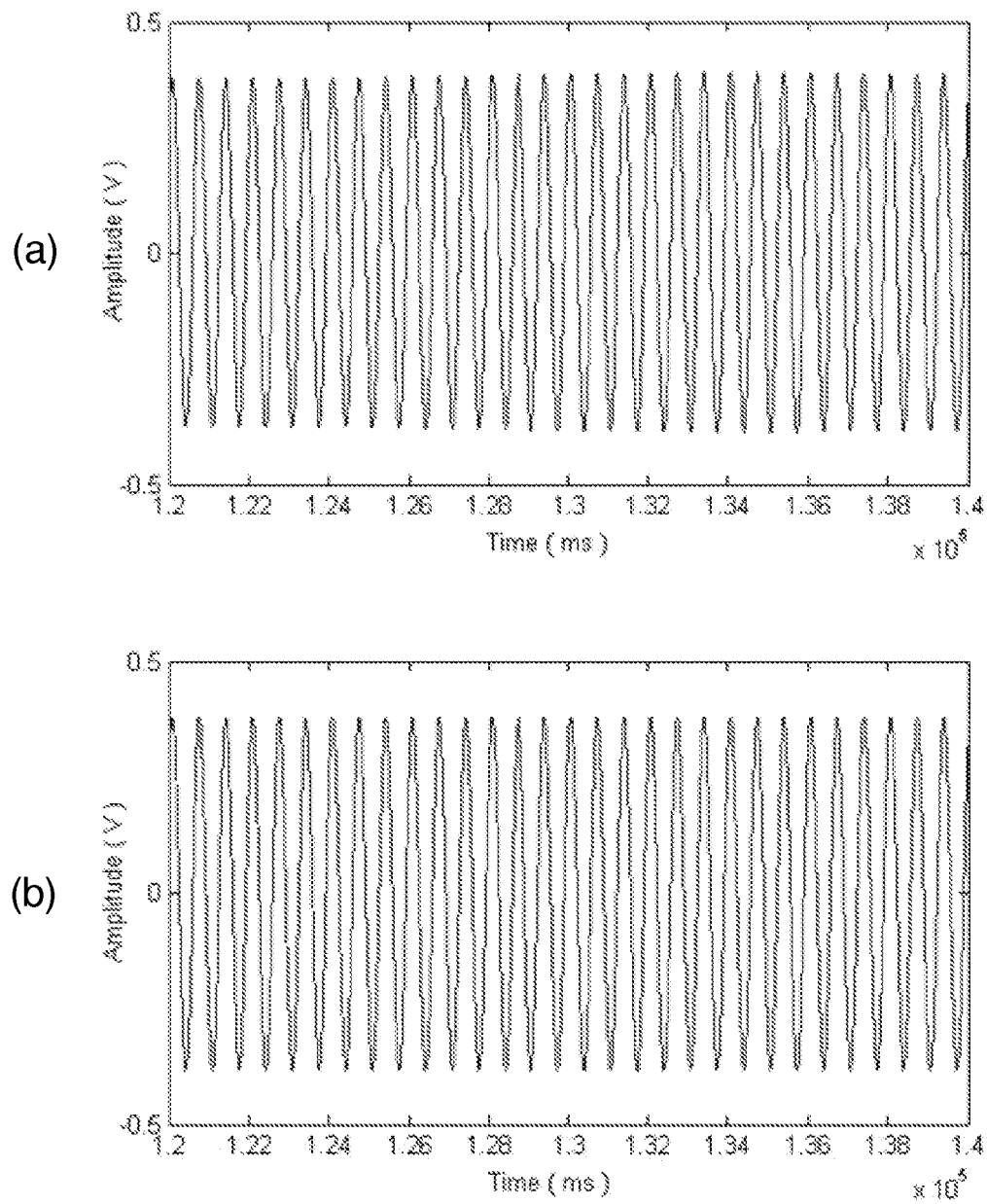
FIGS. 8(a) and 8(b) are plots in the time domain of a pressure signal after processing in a beating detection module in the data analyser of FIG. 5, with and without a heart signal.
Figure 9:
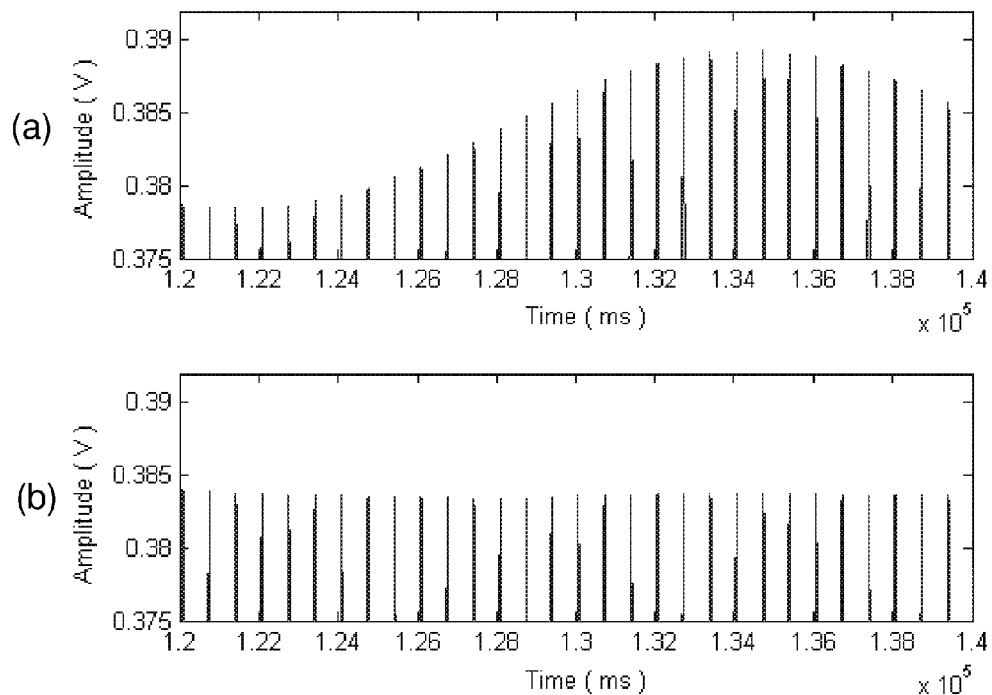
FIGS. 9(a) and 9(b) are enlarged view of the plots in FIGS. 8(a) and 8(b).

FIG. 8($a$) shows a 20 second signal segment which has been filtered with a narrow bandpass surrounding the base frequency of the blood pump at 1.5029 Hz. The filtered signal also contains a heart pulse, which has a frequency shift of 0.037 Hz with respect to the base frequency. The relative magnitude between the blood pump and heart pulse is 40:1. FIG. 8($b$) shows a corresponding filtered signal segment without a heart signal. Although being very small, it is possible to distinguish a difference between the signal segments, where the presence of the heart causes an overlying variation in signal amplitude in FIG. 8($a$) which is lacking in FIG. 8($b$). FIGS. 9($a$) and ($b$) are enlarged views of the signal peaks in FIGS. 8($a$) and 8($b$), respectively, showing a clear difference between the filtered signal segments with and without a heart pulse.

In one embodiment, the beating detection block 53 is configured to detect the beating signal based on an envelope derived from the filtered signal segment.

Figure 10:
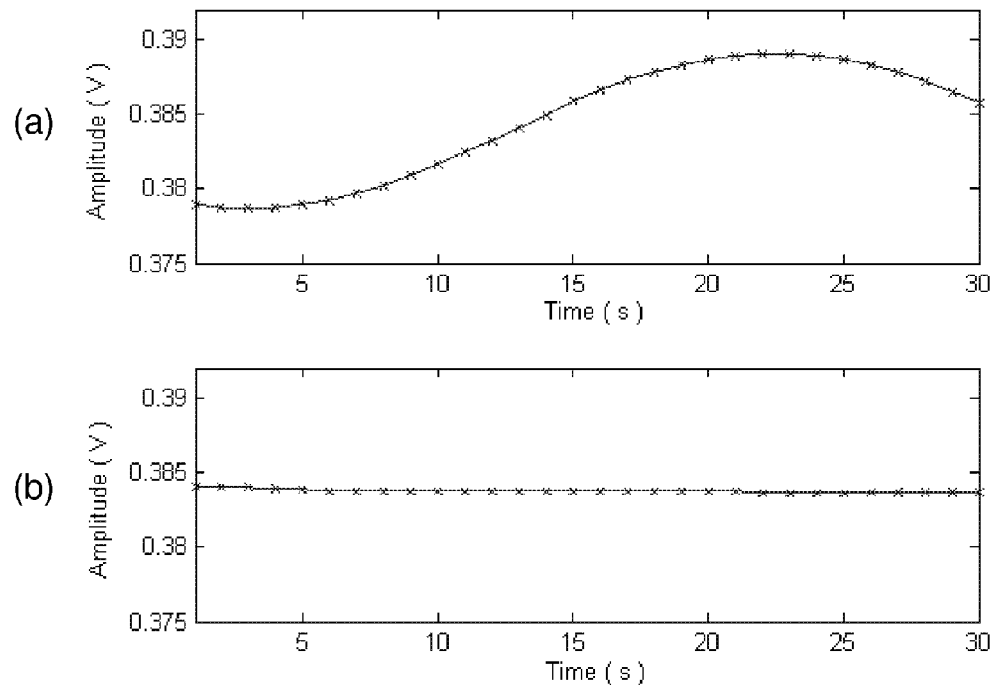
FIGS. 10(a) and 10(b) are plots of envelopes extracted from the data in FIGS. 9(a) and 9(b).

In one such variant, the beating detection block 53 derives the envelope by extracting an array of peak values from the signal segment. The extracted peak values may be given by extracting signal values of individual peaks identified in the signal segment. To improve noise robustness, each extracted peak value may instead be calculated as an average or sum of the signal values forming each peak in the signal segment, e.g. including signal values within 10-25% of the peak value or within a given time range around the peak value. The derived envelope (peak value array) is then processed for calculation of an evaluation parameter. FIGS. 10($a$) and 10($b$) show peak value arrays extracted from FIGS. 9($a$) and 9($b$), respectively.

In another variant, block 53 derives the envelope by applying a linear, time-invariant filter known as a Hilbert transformer to the signal segment s. This operation results in a transformed signal segment š, which is a 90° phase-shifted version of the signal segment. The envelope b(n) can then be derived from $$b(n)=\sqrt{s^2(n)+\check{s}^2(n)},$$

with n being the different positions in the signal segment.

For improved processing efficiency, block 53 may derive an approximate envelope $\hat{b}(n)$ from the signal segment s based on the relation $$\hat{b}(n) = |s(n)| + \frac{2}{\pi}|s(n+1) - s(n-1)|.$$

The derived envelope, be it approximate or not, is then processed for calculation of an evaluation parameter.

In either variant, the derived envelope may be low-pass filtered to further remove envelope noise, before being processed for calculation of the evaluation parameter.

In either variant, the resulting value of the evaluation parameter may be compared to a threshold value for determining presence or absence of a beating signal.

In one example, the evaluation parameter is the absolute sum of derivatives of the values of the envelope, given by:

$$\sum_{n=0}^{N-1} |(b(n+1) - b(n))|$$

with b(n) being the envelope value at position n, and N being the number of values in the envelope.

FIG. 11 illustrates a result of moving a 20 second window over a 5 minute pressure signal, one second at the time, and calculating the absolute sum of derivatives on an envelope derived for each 20-second signal segment. The upper curve is calculated for filtered signal segments containing a heart signal, and the lower curve is calculated for filtered signal segments without a heart signal. Clearly, a threshold value can be defined to distinguish between the presence and absence of a heart signal.

The upper curve exhibits a waveform due to the fact that the signal segment contains part of a full beating signal period. Thus, over time, the signal segments will contain different parts of the beating signal. Since the gradient is small around the peaks and valleys of the envelope and larger therebetween, the calculated sum of derivatives will vary correspondingly over time. It should be realized that, for a given length (time window) of the signal segment, the detectability of the gradients will decrease with decreasing frequency difference between heart and blood pump, since this lowers the beating frequency and flattens the envelope. A wider time window will improve the detectability until the point where the amplitude of the beating becomes smaller than the noise.

In another example, the evaluation parameter is the variance of the values of the envelope. FIG. 12 is a plot corresponding to FIG. 11, but illustrating the variance as a function of time, with (upper) and without (lower) a heart signal. Clearly, a threshold value can be defined to distinguish between the presence and absence of a heart signal.

In yet another example, which may reduce influence of envelope noise, the evaluation parameter is an averaged sum of derivatives, e.g. given by $$\sum_{n=1}^{N-1} \left| \frac{(b(n+1) - b(n-1))}{2} \right|.$$

In another embodiment, the beating detection block 53 determines the presence or absence of a beating signal based on pattern recognition processing. For example, all or part of the signal segment or the envelope may be matched against one or more predetermined signal patterns that are representative of a beating signal. In one example, the derived envelope (optionally low-pass filtered) may be cross-correlated or otherwise convolved with each of a set of sinus waves of different frequencies. Each cross-correlation/convolution results in a correlation curve, from which a maximum correlation value can be derived. The resulting set of maximum correlation values may then be compared to a threshold value for determining presence/absence of a beating signal, where a high enough maximum correlation value may be taken as an indication of such presence.

All of the above examples of determining presence of a beating signal may involve the further step of assessing the reliability of the determined beating signal. This assessment may involve determining the beating frequency of the beating signal and checking if this beating frequency is reasonable. Depending on how the beating signal is identified, the beating frequency may be determined by processing the derived envelope in the time/frequency domain, or by identifying the frequency of the sinus wave that yields the maximum correlation value. The beating frequency may be checked in absolute terms and/or in relation to one or more beating frequencies determined in preceding iterations of the monitoring process (FIG. 4), where large enough deviations from the preceding beating frequency/frequencies may be taken as an indication that the determined beating signal is unreliable. The assessment may result in a reliability score that indicates the reliability of the determined beating signal. Alternatively or additionally, the reliability assessment may include the step of controlling the pump to change its pumping frequency and checking if a corresponding change occurs in the beating signal. For example, the pumping frequency may be shifted slightly, or the pump may be intermittently shut-down. The outcome of the reliability assessment may affect the execution of steps 409-410, e.g. whether an alarm/warning is activated, whether further iterations of the monitoring process is required before activating the alarm/warning, whether the pumping frequency is to be changed, etc.

Tests have shown that different evaluation parameters may be preferable in different situations. For example, the use of variance may increase the detectability when looking for a beating signal around one of the harmonics, whereas the use of absolute sum of derivatives or averaged sum of derivatives may be better when looking for a beating signal around the base frequency. Pattern recognition may be resorted to when other detection methods fail. Thus, the beating detection block 53 may be configured to use one or any combination of these evaluation parameters.

Figure 13:
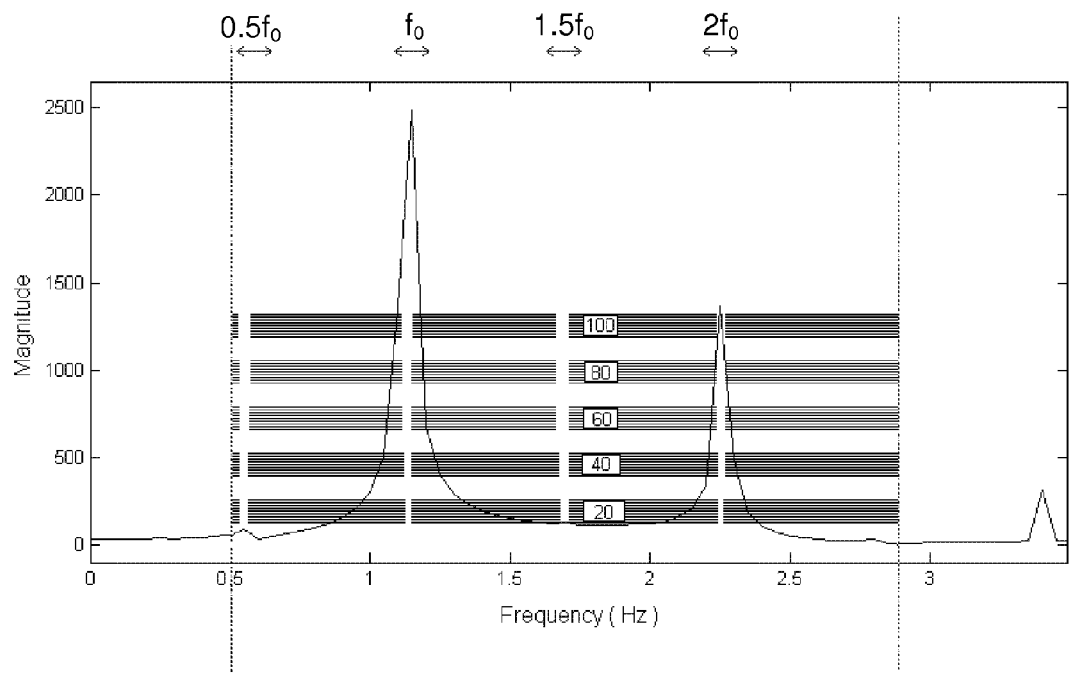
FIG. 13 is a diagram illustrating the performance of a beating detection module, for different relative magnitudes between the blood pulse and the heart pulse.

FIG. 13 is an example of frequency and amplitude ranges in which a heart pulse is detectable using the beating detection block 53. The dotted lines indicate the frequency range of a normal heart, and the dark horizontal bands indicate the frequencies at which a heart pulse could be detected in a system using a pumping frequency of 1.13 Hz. The five rows of horizontal bands represent different relative magnitudes between the blood pump and heart pulses, ranging from 20:1, 40:1, 60:1, 80:1 and 100:1 from the bottom row to the top row. Compared to the corresponding plot in FIG. 7, the blind zones are much smaller, indicating that the beating detection method is superior to the direct detection method when it comes to detecting presence of a heart pulse near the frequency components of the blood pump, especially its base frequency and corresponding harmonics.

Figure 14:
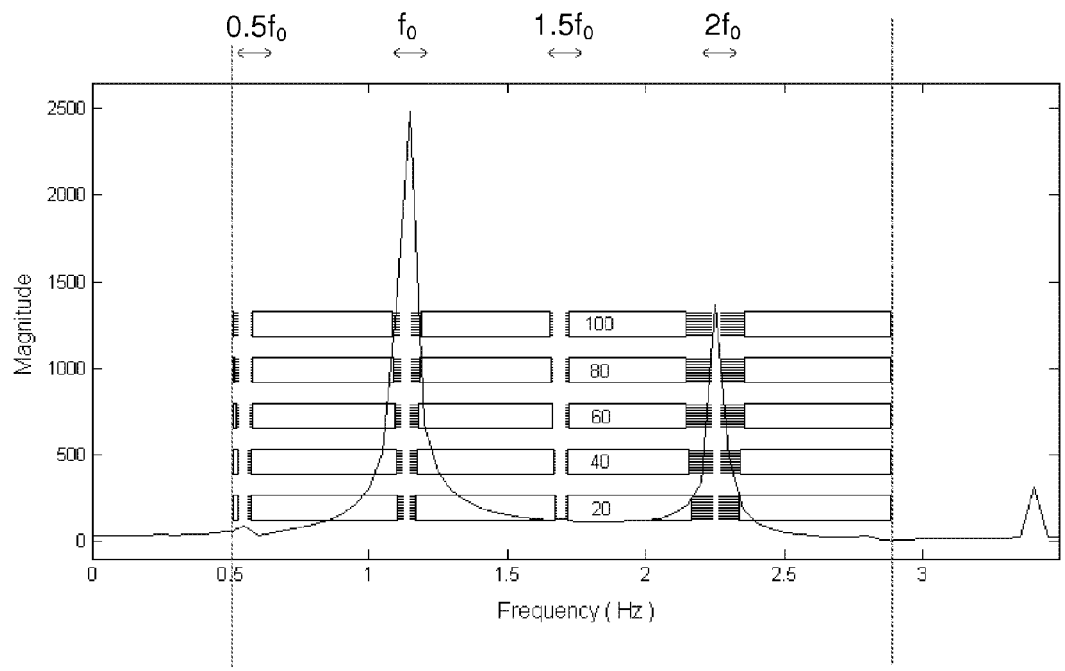
FIG. 14 is a diagram illustrating the performance of combined direct detection and beating detection modules, for different relative magnitudes between the blood pulse and the heart pulse.

Finally, FIG. 14 is a diagram illustrating the performance of the surveillance device in FIG. 5, with combined direct detection and beating detection. The bright bands represent frequency regions in which heart detection is achieved by the direct detection method, whereas the dark bands represent frequency regions in which heart detection is achieved by beating detection. The combination of techniques makes it possible to individually optimize the direct detection method and beating detection method (FIG. 4) for detection in the respective frequency regions.

The invention has mainly been described above with reference to a few embodiments. However, as is readily appreciated by a person skilled in the art, other embodiments than the ones disclosed above are equally possible within the scope and spirit of the invention, which is defined and limited only by the appended patent claims.

For example, the pressure signal may originate from any conceivable type of pressure sensor, e.g. operating by resistive, capacitive, inductive, magnetic or optical sensing, and using one or more diaphragms, bellows, Bourdon tubes, piezo-electrical components, semiconductor components, strain gauges, resonant wires, etc.

Further, the illustrated embodiments are applicable for surveillance of all types of extracorporeal blood circuits in which blood is taken from a patient's circulation to have a process applied to it before it is returned to the circulation. Such blood circuits include hemodialysis, hemofiltration, plasmapheresis, apheresis, extracorporeal membrane oxygenation, assisted blood circulation, and extracorporeal liver support/dialysis.

Further, the monitoring technique is applicable to any type of blood pump that generates pressure pulses in the blood circuit, not only rotary peristaltic pumps as disclosed above, but also other types of positive displacement pumps, such as linear peristaltic pumps, diaphragm pumps, as well as centrifugal pumps.

The skilled person readily realizes that the inventive monitoring technique may be based solely on beating detection. Optionally, beating detection may be combined with another detection technique, such as the above-described direct detection method or pressure level detection using thresholds as described by way of introduction. The combined detection techniques may be carried out in series, in any order, or in parallel.

The skilled person may find other ways of detecting a beating signal in the pressure signal. The above-described selective bandpass filtering around different frequency components of the blood pump is included to facilitate beating detection, but may be dispensed with. The beating signal need not be detected by analysing signal segments in the time domain For example, if the signal segment is long in relation to the period of the beating signal, beating may be detectable in the frequency domain, e.g. following a Fourier transformation of aforesaid envelope.

Figure 15:
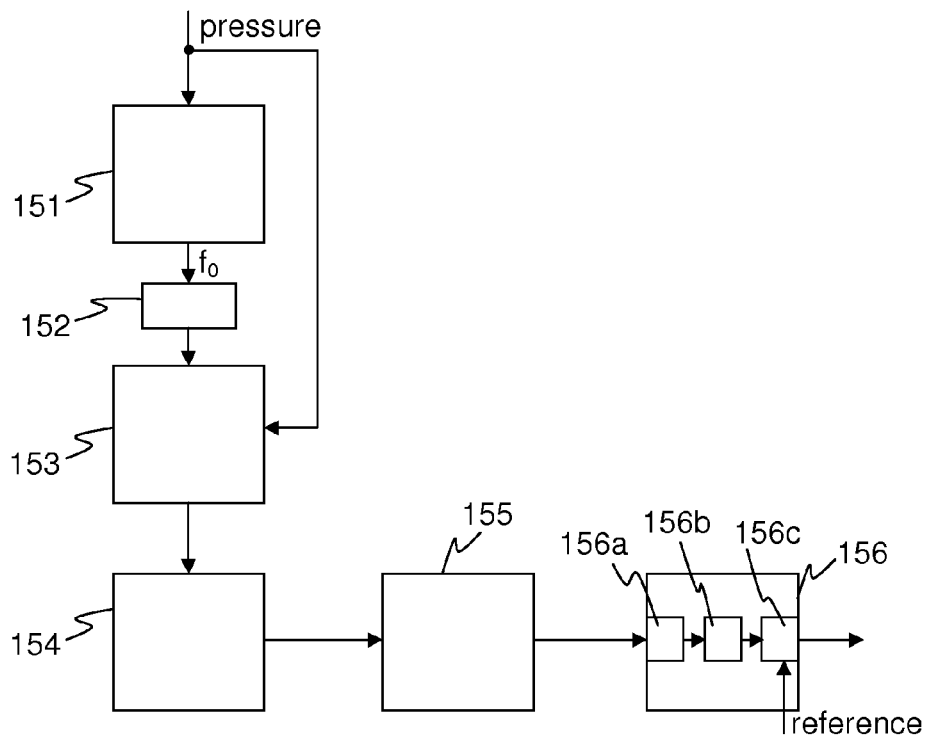
FIG. 15 is a schematic view of an arrangement of analog devices for detection of a beating component in a pressure signal.

Furthermore, the inventive concepts are not limited to digital signal processing. FIG. 15 illustrates an exemplary combination of analog devices for detection of a beating component in a pressure signal. The individual devices are known per se, and alternative implementations are readily available to the skilled person. The exemplary combination of analog devices includes a bandpass filter 151 which is adapted to filter an incoming pressure signal to isolate a signal component at the base frequency ($f_0$) of the pumping device. A frequency multiplier 152 is arranged to receive the filtered pressure signal and is controllable to generate a corresponding output signal at a selected multiple (0.5, 1, 2.5, 3 etc) of the base frequency. The output signal from the multiplier 152 is input as a control signal to a controllable bandpass filter 153, which is adapted to receive and filter the incoming pressure signal. The filter 153 is thereby controlled to process the pressure signal by removing all frequencies except for a frequency band around the frequency of the control signal from the multiplier 152 (cf. step 406 in FIG. 4). The processed pressure signal is input to a peak detector 154 which thereby generates an envelope signal, which in turn is fed to a high-pass filter 155 which removes any DC component from the envelope signal. Optionally, a low-pass filter (not shown) may be included to remove high-frequency noise from the envelope signal. Finally, the envelope signal is received by an amplitude detector 156 which is adapted to determine presence/absence of a beating signal. The amplitude detector may include, in sequence, a full wave rectifier 156a, a low-pass filter 156b and a comparator 156c which is fed with a reference signal. If the amplitude of the input signal to the comparator 156c exceeds the reference signal, the comparator 156c may output a signal indicating presence of a beating signal, otherwise not, or vice versa.

The above-described inventive concepts may also be applicable to monitoring the integrity of flow circuits for transferring other fluids than blood. Likewise, these flow circuits need not be in fluid communication with a patient, but could be connected to any other type of receptacle.

Figure 16A:
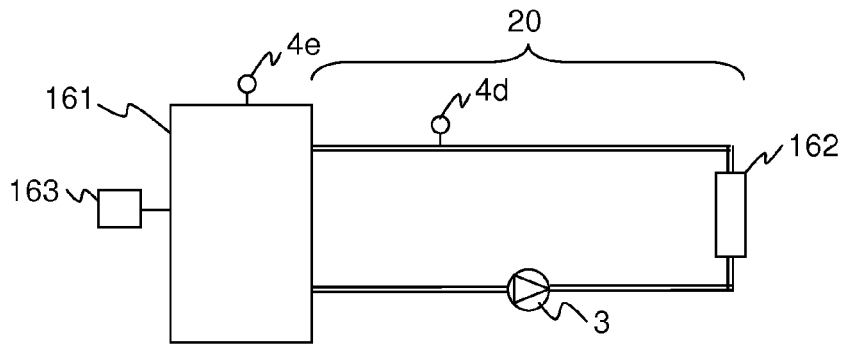
FIGS. 16(a) and 16(b) are schematic views of flow circuit arrangements that may be monitored using embodiments of the invention.

FIG. 16(a) illustrates a flow circuit 20 which is arranged to communicate fluid from a first receptacle 161 through a second receptacle 162 back to the first receptacle 161. The second receptacle 162 may be arranged to process the fluid (like the dialyser 6 in FIG. 1). Alternatively, the second receptacle 162 may be treated (cleaned, purged, disinfected, etc) by the circulating fluid. A pumping device 3 circulates the fluid in the circuit 20. A pressure sensor 4d or 4e is arranged to indicate the fluid pressure in the first receptacle 161 or the flow circuit 20. A pulse generator 163 is associated with the first receptacle 161 so as to generate pressure waves in the fluid therein. The pulse generator 163 may be inherent to the first receptacle 161 (similarly to the heart of a patient), e.g. in the form of a pump, a vibrator, etc. Alternatively, the pulse generator 163 may be a separate dedicated device which is attached to the first receptacle 161, such as a vibrator, ultrasound generator, etc. Interference between pressure waves generated by the pulse generator 163 and pressure waves generated by the pumping device 3 will form a beating in a pressure signal detected by either the pressure sensor 4d connected to the flow circuit 20 or the pressure sensor 4e connected to the first receptacle 161. As described in the foregoing, the pressure signal may be analyzed by a monitoring device (not shown) for determining the integrity of the flow circuit 20 based at least partly on the presence or absence of the beating in the pressure signal. In this, and in all other embodiments disclosed herein, the monitoring device may operate on pressure signals from more than one pressure sensor.

Figure 16B:
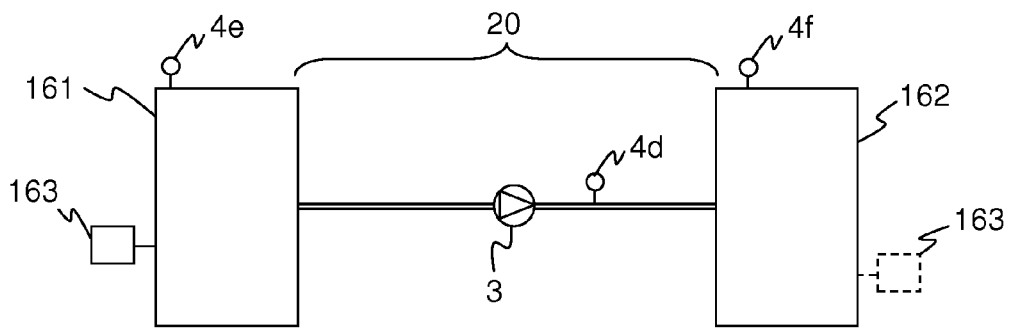

FIG. 16(b) illustrates a flow circuit 20 which is arranged to communicate fluid along a one-way path from a first receptacle 161 to a second receptacle 162. Like in FIG. 16(a), a pulse generator 163 may be associated with the first receptacle 161, and the integrity of the flow circuit may be determined by a monitoring device (not shown) based at least partly on the presence or absence of the beating in a pressure signal. The pressure signal may be given by a pressure sensor 4d-4f connected to the first receptacle 161, the flow circuit 20 or the second receptacle 162. In an alternative embodiment, the pulse generator 163 may be associated with the second receptacle 162, as indicated by dashed lines in FIG. 16(b).

The arrangements of FIGS. 16(a) and 16(b) could be used with any type of fluid, typically a liquid, which is communicated to or through the second receptacle 162.

In one such example, the arrangement of FIG. 16(a) illustrates a flow circuit in which blood is pumped from a container/machine 161 through a blood processing device 162 and back to the container/machine 161. Although it is not shown in FIG. 16(a), the blood could instead be directed to another container/machine downstream of the blood processing device 162. The blood processing device 162 could be any known device configured to modify and/or analyse the blood.

In a further example, the second receptacle 162 is a dialyser which is reprocessed by pumping water, optionally together with suitable chemicals, from the first receptacle 161 through the dialyser 162. The flow circuit may be closed, as in FIG. 16(a), or open-ended, as in FIG. 16(b). An example of a closed-circuit dialyser reprocessing system is known from US2005/0051472.

In another example, the arrangement of FIG. 16(a) depicts part of a dialysate regeneration system, in which dialysate is circulated from a dialysate supply 161 through a dialysate regeneration device 162 and back to the supply 161. An example of a dialysate regeneration device is known from WO 05/062973.

In yet another example, FIGS. 16(a) and 16(b) illustrate arrangements for priming an extracorporeal blood circuit by pumping a priming fluid from a supply 161 via the flow circuit 20 to a dialyser 162. The priming fluid may e.g. be dialysate, saline, purified water, etc.

In a still further example, FIGS. 16(a) and 16(b) illustrate arrangements for cleaning and disinfecting the dialysate flow path of a dialysis machine, by pumping a cleaning fluid via a flow path 20 to a dialyser/dialyser tubing 162. The cleaning fluid may e.g. be hot water, a chemical solution, etc.

In a further example, FIGS. 16(a) and 16(b) illustrate arrangements for purifying water, by pumping water from a supply 161 through a purifying device 162. The purifying device 162 may use any known water purification technique, e.g. reverse osmosis, deionization or carbon absorption.

In another example, FIGS. 16(a) and 16(b) illustrate arrangements for providing purified water to a dialysis machine 162, e.g. to be used in the preparation of dialysate therein.

In all of these examples, and in other applications related to medical treatment of human or animal patients, it may be vital to monitor the integrity of the flow circuit 20. Such monitoring can be accomplished according to the inventive concepts disclosed herein.

The invention claimed is:

1. A method for monitoring the integrity of a flow circuit in fluid communication with a receptacle, said flow circuit comprising a pumping device configured to transfer fluid through the flow circuit, said method comprising:
   receiving a pressure signal from a pressure sensor, said pressure signal being indicative of fluid pressure in the receptacle or the flow circuit,
   analyzing the pressure signal for a beating signal formed by interference between pressure waves generated by a pulse generator associated with the receptacle and pressure waves generated by the pumping device, and
   determining the integrity of the flow circuit based at least partly on the presence or absence of the beating signal.

2. The method of claim 1, wherein the beating signal is detected by analyzing the pressure signal in a time domain.

3. The method of claim 1, further comprising obtaining one or more specific frequencies related to a pumping frequency of the pumping device, and wherein said analyzing comprises creating at least one filtered pressure signal in which all but one of said specific frequencies are removed.

4. The method of claim 3, wherein said at least one specific frequency comprises one or more of: half the pumping frequency, the pumping frequency, and harmonics of the pumping frequency.

5. The method of claim 3, wherein said analyzing comprises determining an envelope of the filtered pressure signal.

6. The method of claim 5, wherein determining the envelope comprises extracting an array of temporally sequential peak values from the filtered pressure signal.

7. The method of claim 5, wherein said analyzing further comprises calculating at least one of a sum of derivatives and a variance based on the envelope.

8. The method of claim 3, further comprising: matching at least part of the filtered pressure signal against one or more predetermined signal patterns so as to detect the beating signal.

9. The method of claim 3, wherein said obtaining comprises at least one of analyzing the pressure signal in a frequency domain to identify said one or more specific frequencies, deriving a frequency measurement signal from the pumping device, and deriving a set value of a controller configured to control the pumping frequency of the pumping device.

10. The method of claim 1, further comprising: processing the pressure signal for detection of a signal component generated by the pulse generator, wherein said determining the integrity of the flow circuit is also based on the presence or absence of said signal component.

11. The method of claim 10, wherein said analyzing of the pressure signal for detection of a beating signal is conditioned upon absence of said signal component in the pressure signal.

12. The method of claim 1, further comprising:
    causing, in the absence of a beating signal, a predetermined change in the pumping frequency of the pumping device.

13. The method of claim 1, further comprising: causing the pumping device to be temporarily inactivated, identifying the frequency of the pulse generator, and causing the pumping device to be activated with such a pumping frequency that all of a plurality of associated frequency components are offset from the frequency of the pulse generator.

14. The method of claim 1, wherein said analyzing is effected on a sequence of partially overlapping signal segments of said pressure signal, the length of each segment being given by a predetermined time window.

15. A computer program product comprising instructions for causing a computer to perform the method of claim 1.

16. A method for monitoring the integrity of an extracorporeal blood flow circuit connected to a blood vessel of a patient, said extracorporeal blood flow circuit comprising a blood pumping device, said method comprising:
    receiving a pressure signal from a pressure sensor in the blood flow circuit,
    analyzing the pressure signal for a beating signal formed by interference between pressure waves generated by the patient's heart and pressure waves generated by the blood pumping device, and
    determining the integrity of the blood flow circuit based at least partly on the presence or absence of the beating signal.

17. A device for monitoring the integrity of a flow circuit in fluid communication with a receptacle, said flow circuit comprising a pumping device for transferring fluid through the flow circuit, said device comprising:
    an input for a pressure signal from a pressure sensor, said pressure signal being indicative of fluid pressure in the receptacle or the flow circuit, and
    a signal processor comprising a first module configured to analyze the pressure signal for a beating signal formed by interference between pressure waves generated by a pulse generator associated with the receptacle and pressure waves generated by the pumping device, said signal processor being configured to determine the integrity of the flow circuit based at least partly on the presence or absence of the beating signal.

18. The device of claim 17, wherein the first module is configured to detect the beating signal by analyzing the pressure signal in a time domain.

19. The device of claim 17, wherein the first module is further configured to obtain one or more specific frequencies related to a pumping frequency of the pumping device, and to create at least one filtered pressure signal in which all but one of said specific frequencies are removed.

20. The device of claim 19, wherein the first module is further configured to determine an envelope of the filtered pressure signal.

21. The device of claim 20, wherein the first module is further configured to determine the envelope by extracting an array of temporally sequential peak values from the filtered pressure signal.

22. The device of claim 20, wherein the first module is further configured to calculate at least one of a sum of derivatives and a variance based on the envelope.

23. The device of claim 19, wherein the first module is further configured to match at least part of the filtered pressure signal against one or more predetermined signal patterns so as to detect the beating signal.

24. The device of claim 17, wherein the signal processor comprises a second module configured to process the pressure signal for detection of a signal component generated by the pulse generator, wherein the signal processor is configured to determine the integrity of the flow circuit also based on the presence or absence of said signal component.

25. The device of claim 24, wherein the signal processor is configured to operate the first and second modules in sequence, such that the first module is operated only when the second module fails to detect said signal component in the pressure signal.

26. The device of claim 17, wherein the signal processor is configured to cause, in the absence of a beating signal, a predetermined change in the pumping frequency of the pumping device.

27. The device of claim 17, wherein the signal processor is configured to cause the pumping device to be temporarily inactivated, to identify the frequency of the pulse generator, and to cause the pumping device to be activated with such a pumping frequency that all of a plurality of associated frequency components are offset from the frequency of the pulse generator.

28. An apparatus for extracorporeal blood treatment, comprising an extracorporeal blood flow circuit including a blood pumping device, a pressure sensor arranged in the blood flow circuit, and the device of claim 17.

29. A device for monitoring the integrity of a flow circuit in fluid communication with a receptacle, said flow circuit comprising a pumping device for transferring fluid through the flow circuit, said device comprising:
- means for receiving a pressure signal from a pressure sensor, said pressure signal being indicative of fluid pressure in the receptacle or the flow circuit,
- means for analyzing the pressure signal for a beating signal formed by interference between pressure waves generated by a pulse generator associated with the receptacle and pressure waves generated by the pumping device, and
- means for determining the integrity of the flow circuit based at least partly-on the presence or absence of the beating signal.

30. A device for monitoring the integrity of an extracorporeal blood flow circuit connected to a blood vessel of a patient, said extracorporeal blood flow circuit comprising a blood pumping device, said device comprising:
- means for receiving a pressure signal from a pressure sensor in the blood flow circuit,
- means for analyzing the pressure signal for a beating signal formed by interference between pressure waves generated by the patient's heart and the blood pumping device, and
- means for determining the integrity of the blood flow circuit based at least partly on the presence or absence of the beating signal.

* * * * *

UNITED STATES PATENT AND TRADEMARK OFFICE
CERTIFICATE OF CORRECTION

PATENT NO. : 8,718,957 B2  Page 1 of 1
APPLICATION NO. : 12/988146
DATED : May 6, 2014
INVENTOR(S) : Furmanski et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 730 days.

Signed and Sealed this

Twenty-ninth Day of September, 2015

Michelle K. Lee
*Director of the United States Patent and Trademark Office*